United States Patent [19]

Tinker

[11] 4,072,709

[45] Feb. 7, 1978

[54] PRODUCTION OF LACTIC ACID

[75] Inventor: Harold Burnham Tinker, Creve Coeur, Mo.

[73] Assignee: Monsanto Company, St. Louis, Mo.

[21] Appl. No.: 581,245

[22] Filed: May 27, 1975

[51] Int. Cl.$^2$ ............................................ C07C 59/08
[52] U.S. Cl. ........................... 260/535 R; 260/530 R; 560/103; 560/232; 560/238
[58] Field of Search ..................................... 260/535 R

[56] References Cited

U.S. PATENT DOCUMENTS

| | | | |
|---|---|---|---|
| 2,909,538 | 10/1959 | Kirshenbaum | 260/535 |
| 3,257,459 | 6/1966 | Swakon | 260/535 |

FOREIGN PATENT DOCUMENTS

| | | |
|---|---|---|
| 980,239 | 1/1965 | United Kingdom. |

OTHER PUBLICATIONS

Adkins & Krsek, J. Amer. Chem. Soc., 71 3051–3055, (1949).
Cram & Hammond, Org. Chemistry, 2nd Ed., pp. 547, 355–356, 1964.

*Primary Examiner*—Paul J. Killos
*Attorney, Agent, or Firm*—Howard C. Stanley

[57] ABSTRACT

Lactic acid is synthesized by a process in which a vinyl ester is hydroformylated to an α-substituted propionaldehyde by reacting the vinyl ester with carbon monoxide and hydrogen in the presence of a hydroformylation catalyst and by further converting the α-substituted carbonyl intermediate via oxidation and hydrolysis to lactic acid.

A preferred embodiment of the invention utilizes vinyl acetate as the feed.

24 Claims, No Drawings

PRODUCTION OF LACTIC ACID

The present invention is directed to a process for preparing lactic acid by hydroformylating a vinyl ester of a carboxylic acid (herein also referred to as vinyl carboxylates) with carbon monoxide and hydrogen to prepare an alpha-acyloxypropionaldehyde, and oxidizing and hydrolyzing to obtain lactic acid.

BACKGROUND OF THE INVENTION

Lactic acid is widely used as a food ingredient. Lactic acid has in the past been available by fermentation processes utilizing carbohydrates as raw material. In recent years an industrial process has utilized the reaction of hydrogen cyanide with acetaldehyde, followed by the hydrolysis of the resulting lactonitrile employing hydrochloric acid as catalyst. While this route is useful and less costly than the older fermentation process, it will be recognized that there is danger and expense associated with the use of hydrogen cyanide, and an alternate route is therefore desirable. In particular, the lactonitrile route involves cyanide which is highly poisonous and great care must be taken in the manufacturing process to ensure that no cyanide remains in the final product before it can be used as a food ingredient. Also, the process involves highly corrosive chloride which requires expensive materials of construction. A number of possible routes to lactic acid from such fundamental starting materials as olefins, carbon monoxide, water, hydrogen, oxygen, etc. and their reaction products can be visualized, but most such routes are impractical or inoperative. For example, acetaldehyde is available commercially, and carboxylation of acetaldehyde by reaction with carbon monoxide and water has been reported to produce lactic acid (*J.Applied Chem.*, 20, page 7, (1970)), but attempts in our laboratory to use this procedure have resulted in only traces of lactic acid. While the industrial cyanohydrin route to lactic acid has some undesirable cost factors, it is nevertheless an operative, reasonably efficient route which utilizes available raw materials. It follows that for industrial use a new route will need to have fairly high conversions to the desired lactic acid product, or that product along with useful and marketable concomitant products.

Accordingly, it is an object of the present invention to provide a synthetic route to lactic acid which does not require any cyanide and which does not involve corrosive reactants.

It is a further object of the present invention to provide a synthetic process for lactic acid manufacture which requires only cheap, readily available starting materials.

It is a further object of the present invention to provide a process for lactic acid production which involves very simple and inexpensive by-product separation procedures.

It is a further object to provide a route to lactic acid which obtains sufficient yields of desired useful intermediates and by-products and utilizes efficient conversion and separation procedures so as to be technologically and economically practical in terms of cost and efficiency factors with respect to raw materials and conversion procedures.

Hydroformylation processes are well known in the art and have been directed to the production of reaction mixtures comprising substantial amounts of aldehydes and alcohols by the reaction of olefins with carbon monoxide and hydrogen at elevated temperatures and pressures in the presence of certain catalysts. The prior art teaches the use of dicobalt octacarbonyl or its various modified forms as well as carbonyls of other Group VIII metals such as rhodium, ruthenium, and iridium which may also be modified by ligands comprised of organic compounds of Group V elements such as triaryl- and trialkyl-phosphines, arsines, etc. Certain disadvantages are potentially present in the hydroformylation processes described in the prior art when they are applied to a vinyl ester as the reactant. In particular, if it is desired to synthesize lactic acid by the route described herein, a high selectivity to alpha-acyloxypropionaldehyde in the hydroformylation reaction step is required for a commercially competitive process. Thus, Adkins and Krsek (J Amer. Chem. Soc., 71, 3051 (1949) ) studied the hydroformylation of vinyl acetate with cobalt carbonyl as the catalyst at 125° and under a pressure of 4600 psi of a 1:1 mixture of carbon monoxide and hydrogen. They obtained a 30% yield of alpha-acetoxypropionaldehyde and a 22% yield of beta-acetoxypropionaldehyde. By contrast, the hydroformylation process in accordance with procedures described herein gives yields of over 70% of the alpha-acetoxypropionaldehyde, thus, leading to good yields of lactic acid.

SUMMARY OF THE INVENTION

It has now been found that lactic acid can efficiently be produced in accord with the following:

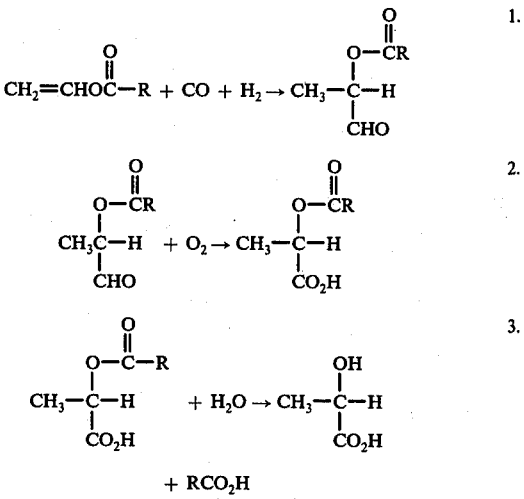

The order of the reactions 2 and 3 can be reversed, or the oxidation and hydrolysis can be carried out simultaneously.

In the above equations R is an organic radical constituting the residue of an organic acid, such as formic acid, acetic acid, propionic acid, benzaic acid, etc., with the R ordinarily being an alkyl or aryl group, or any organic hydrocarbyl radical, for example an alkyl group of 1 to 6 carbon atoms, phenyl, tolyl, etc. Vinyl carboxylates in general can be employed in the present process, but ordinarily there is no advantage in utilizing a vinyl ester other than an ester of one of the simple organic acids. The carboxylate portion of the vinyl ester does not constitute part of the lactic acid product in any event. Vinyl acetate is a suitable vinyl carboxylate which can be prepared by known procedures from acetylene or ethylene and acetic acid, and vinyl acetate will generally be used in the present invention. Therefore vinyl acetate will be used in most of the exemplifications and discussion herein. However, it is to be understood that any of the other vinyl carboxylates can be substituted for vinyl acetate in the examples and otherwise herein.

In the illustrated reaction 1 (R=CH$_3$), the product is shown as alpha-acetoxypropionaldehyde, and in accordance with the present invention it has been found possible to obtain this product in high yield by the use of suitable hydroformylation catalysts. In this type of procedure it is also possible to produce beta-acetoxypropionaldehyde, or to hydrogenate the vinyl acetate to ethyl acetate, but fortunately conditions have been found which give high yields of the alpha-acetoxypropionaldehyde.

In carrying out the present invention, any hydroformylation conditions can be used which result in appreciable yields of alpha-acetoxypropionaldehyde, and hydroformylation conditions using Group VIII metal catalysts such as rhodium, ruthenium, iridium, cobalt, iron and palladium are well known. However, there will be advantage in obtaining high yields of alpha-acetoxypropionaldehyde, and this may be virtually necessary to make the process industrially practical. The extent to which production of concomitant products can be tolerated depends upon the particular products and their usefulness and marketability, but in general it will be advantageous to obtain high yields of alpha-acetoxy-propionaldehyde, such as at least 70% or more preferably at least 80%, based on the vinyl carboxylate reacted. Thus in one aspect the present invention involves reacting vinyl acetate with hydrogen and carbon monoxide in a manner to promote selective production of alpha-acetoxy-propionaldehyde. It will be advantageous to employ conditions which promote the production of aldehydes rather than of alcohols or alkyl acetates and therefore to use hydroformylation catalysts recognized as being low in hydrogenating ability with a general preference for rhodium catalysts, and for the less basic ligands, such as aryl phosphine or arsine ligands, rather than the alkyl phosphine and arsine ligands. Cobalt and various other hydroformylation catalysts can be used in the invention but it may be necessary to utilize more carefully selected conditions of temperature, pressure, concentrations, etc. to obtain appreciable yields of the desired alpha-acetoxypropionaldehyde. Further description of hydroformylation catalysts useful herein, and guidance on selection of appropriate constituents and conditions to produce aldehyde products, can be found in "Recent Developments in Hydroformylation Catalysis" by F.E. Paulik (*Catalysis Reviews*, 6, 49 (1972)).

In the hydroformylation of vinyl acetate, some beta-acetoxy-propionaldehyde may be produced, but the compound is very unstable under the particular reaction conditions described herein and fortunately is not found as a product of the hydroformylation, as it would be difficult to separate from its isomer. Under the conditions utilized herein it apparently decomposes to acrolein, which is then hydrogenated to propionaldehyde. The latter compound can then be oxygenated to produce propionic acid. Thus, in one aspect, the present invention involves a procedure for converting vinyl acetate to lactic acid, in which the vinyl acetate is hydroformylated to alpha-acetoxypropionaldehyde and beta-acetoxypropionaldehyde and the latter compound is then decomposed and hydrogenated to propionaldehyde, and the mixture of propionaldehydes is then oxidized to obtain acetyl lactic acid and propionic acid. The reactions can be illustrated

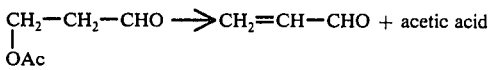

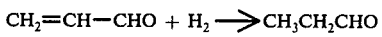

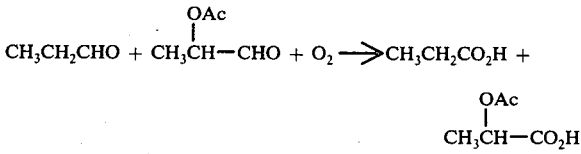

with Ac in the equations representing an acetyl radical. The acetyl radical can then be hydrolyzed from the acetyl lactic acid to yield lactic acid. If desired, the hydrolysis can be conducted prior to the oxidation, with the oxidation then being of a mixture including alpha-hydroxypropionaldehyde and propionaldehyde. The fact that propionaldehyde is produced rather than beta-acetoxy-propionaldehyde in the hydroformylation is very fortunate, as the aldehyde or its oxidation product are useful materials and are amenable to separation from the corresponding hydroxy or acyloxy propionaldehydes or acids, and propionaldehyde or propionic acid for example can be readily separated by distillation from the higher boiling alpha-acetoxypropionaldehyde, lactic aldehyde and lactic acid. Propionaldehyde and propionic acid are useful and desirable products. It has been unexpectedly found that high selectivity to alpha-aceloxypropionaldehyde in the hydroformylation of vinyl esters can be obtained by using as a catalyst system, a rhodium compound together with a biphyllic ligand such as a triaryl- or trialkyl-phosphine, arsine or stibine or a triaryl-phosphite. This catalyst system can be employed in a dissolved form in a suitable solvent, or as a solid by using an insoluble polymeric ligand complexed with the rhodium compound. Preferred forms of the rhodium comound are these which do not contain halide and particularly preferred forms are cationic complexes of rhodium.

Ordinarily the second step in the process for lactic acid synthesis of the present invention is oxidation of an aldehyde group to an acid group. It has been found that alpha-acyloxy-propionaldehyde is an unusually reactive molecule and can be readily oxidized by air or oxygen at room temperature. This very mild oxidation to the alpha-acyloxypropionic acid can be accomplished without a catalyst, although oxidation catalysts such as silver oxide, vanadium oxide and salts, etc., can be used to increase the reaction rate if desired.

Then the third and final step in the process for lactic acid synthesis involves a hydrolysis of alpha-acyloxy-propionic acid to a mixture of lactic acid and carboxylic acid (this carboxylic acid will be acetic acid if vinyl acetate is the starting material for the overall process). This ester hydrolysis step may be conducted in the presence of acid or base catalysts. Quite unexpectedly, however, it has been found that the hydrolysis will also proceed at good rates in the absence of catalysts. While the mechanism of this unusual non-catalyzed ester hydrolysis reaction is now known, it is possible that the acid group on the acyloxypropionic acid is sufficiently activated that it acts as its own acid catalyst in the reaction.

DETAILED DISCLOSURE

Suitable reaction conditions for the three steps of the process will now be given in greater detail.

Step 1—Hydroformylation of Vinyl Ester to alpha-Acyloxypropionaldehyde

Rhodium is the preferred metal component of the hydroformylation catalyst and rhodium catalyst will generally be used for illustration in the following description.

In order to achieve high selectivity to α-acyloxypropionaldehyde in the hydroformylation of vinyl esters with carbon monoxide and hydrogen, it has been found desirable to conduct the reaction at a total pressure of from 4.6 to 175 kg/cm² (65 psig to 2500 psig) and preferably at a total pressure of 32.5 to 140 kg/cm² (460 to 2000 psig). The reaction temperature should be 40° to 160° C and preferably 60° to 125° C. The reaction should be conducted in the presence of a catalyst which is provided by a rhodium compound together with an excess (at least 2 moles per mole of rhodium compound) of a biphyllic ligand where the biphyllic ligang is a tertiary organo-phosphorus compound having 3 to 90 carbon atoms, a tertiary organo-arsenic compound having 3 to 90 carbon atoms, or a tertiary organo-antimony compound having 3 to 90 carbon atoms. Preferred rhodium compounds are those which do not contain halide ion, since the presence of halide increases corrosion in the system and appears to result in decreased rtes of reaction to the desired product. A particularly preferred form of rhodium compound is that of a cationic rhodium complex with a non-coordinating anion. This particular form is simple to prepare, gives very good rates of reaction, and results in very high selectivity to the desired product. Examples of such preferred cationic complexes are $[Rh(CO)_3(Ph_3P)_2]^+[BPh_4]^-$ and $[Rh(CO)_3(Et_3P)_2]^+[ClO_4]^-$.

The rhodium compound is normally provided in a form which is soluble in the liquid reaction medium. The proportions of the rhodium catalyst in the reaction zone relative to the vinyl ester feed are not particularly critical. In general, higher concentration of catalysts produce a faster reaction rate. Concentrations of compounds or complexes in the liquid phase between $10^{-6}$ moles/liter and $10^{-1}$ moles/liter can be used. Another embodiment of the present invention is to provide the catalyst as an insoluble compound containing rhodium by complexing the rhodium with an insoluble polymeric form of the biphyllic ligand.

In a preferred practice of this invention it is advantageous to add an additional amount of biphyllic ligand to the reaction medium in excess of that required to form a stoichiometric rhodium comound or complex containing that ligand, so as to improve catalyst life and to improve selectivity to the desired α-acyloxypropionaldehyde. A preferred concentration range of the biphyllic ligand in the reaction medium is 0.0001 molar to 1.0 molar and an especially preferred range is 0.001 molar to 0.1 molar.

The term biphyllic ligand used throughout this specification means a tertiary organo phosphorus compound, or a tertiary organo arsenic compound, or a tertiary organo antimony compound. This compound is either coordinated to the central rhodium atom to form the coordination complex, or is present as the free compound, i.e., uncoordinated, in the reaction solution containing the rhodium coordination complex. In this latter case the compound has the potential to become coordinated to the central rhodium atom via a ligand exchange reaction with a modifying ligand already coordinated to the central rhodium atom.

Suitable organo-phosphorous, organo-arsenic and organo-antimony biphyllic ligands which may comprise part of the rhodium coordination compound of this invention are those containing trivalent phosphorus, arsenic, or antimony atoms, and are referred to in this specification as phosphines and phosphites, arsines and arsenites, and stibines and stibites, respectively.

In this group of suitable biphyllic ligands, the individual phosphorous, arsenic, and antimony atoms have one available or unshared pair of electrons. An organic derivative of the phosphorus, arsenic, or antimony with the foregoing electronic configuration is, therefore, a suitable ligand for the rhodium containing catalyst of this invention. Organic radicals of any size and composition may be bonded to the phosphorus, arsenic, or antimony atoms, and the radicals are preferably selected from the group consisting of aryl, aryloxy, alkyl, and alkoxy groups. The more preferred ligands are those consisting of at least one but preferably two or three aryl- and/or aryloxy groups as the organic moieties. For example, preferred biphyllic ligands are illustrated by the following structural formulae $MR_3$ where M is P, As, or Sb, and R is e.g. phenyl $(C_6H_5-)$, phenoxy $(C_6H_5O-)$, or tolyl $[CH_3(C_6H_4)-]$, xylyl $(CH_3 \cdot C_6H_3 \cdot CH_3-)$, e.g., $P(C_6H_5)_3$, $P(C_6H_5O)_3$, $As(C_6H_5)_3$, $Sb(C_6H_5)_3$, $P[CH_3(C_6H_4)]_3$.

The more preferred group of biphyllic ligands includes the triphenylphosphines, triphenylphosphites, triphenylarsines, and triphenylarsenites. The preferred component is the aryl or aryloxy group, e.g., the phenyl or phenoxy radical. However, the molecule may also contain some aryl groups in addition to the aryloxy radical.

The modifying ligands, and, if desired, other ligands, satisfy the coordination number of the central rhodium atom, and thus form a rhodium-containing complex. The term coordination compound or coordination complex means a compound or complex formed by combination of one or more electronically rich molecules or atoms, e.g. triphenylphosphine, carbon monixide, 1,5-cyclo-octadiene, (herein also called "COD"), with one or more electronically poor molecules or atoms, e.g. rhodium.

In carrying out the hydroformylation reaction, it is necessary to supply one mole of carbon monoxide and one mole of hydrogen for each mole of vinyl carboxylate converted to acyloxy aldehyde. Excess carbon monoxide or hydrogen over the stoichiometric amounts, however, may be and ordinarily is present, with ratios of $H_2$ to CO varying widely, for example from 10:1 to 1:10 on a mole basis.

It is preferred to use herein a cationic rhodium containing compound as catalyst, such catalyst being an ionic rhodium compound with a rhodium-containing cation having rhodium complexed with ligands other than halide, and a non-coordinating anion. These have the general formula $RhL_xAn$. In this formula, the cationic rhodium moiety is $RhL_x^+$ and the non-coordinating anionic moiety $An^-$ is exemplified by $BPh_4^-$, $BF_4^-$, $ClO_4^-$, $PF_6^-$, $NO_3^-$, and $SiF_6^{2-}$.

In the above formulae L is a ligand, (either the same or different ligands as described herein) and x varies from 2 to 5. The ligand L may or may not be a modifying ligand. For example, in the case where [Rh(Ph$_3$P)$_5$]$^+$ is employed as the rhodium-containing cation, Ph$_3$P is the ligand L and it is also a modifying ligand. In the case where [Rh(COD)(Ph$_3$P)$_2$]$^+$ is employed as the rhodium-containing cation Ph$_3$P and COD are the ligands L, but only Ph$_3$P is a modifying ligand. Finally, in the case where [Rh(COD)$_2$]$^+$ is employed as the rhodium-containing cation, COD is the ligand L, and at least two moles of a modifying ligand such as Ph$_3$P furnished to the reaction solution per mole of rhodium to obtain the catalyst of the present invention. In cases where the ligand L is not a modifying ligand, then it is a ligand displaceable by carbon monoxide under reaction conditions, e.g., COD. Examples of the ligand L include:

mono-enes of 2 to 12 carbon atoms,
dienes of 4 to 12 carbon atoms,
trienes of 6 to 16 carbon atoms,
alkynes of 2 to 12 carbon atoms,
ketones of 3 to 12 carbon atoms,
nitriles of 2 to 12 carbon atoms,
N-alkylamides of 2 to 12 carbon atoms,
N,N-dialkylamides of 3 to 12 carbon atoms,
sulfoxides of 2 to 12 carbon atoms,
tertiary organo phosphorus compounds of 3 to 90 carbon atoms,
tertiary organo arsenic compounds of 3 to 90 carbon atoms,
tertiary organo antimony compounds of 3 to 90 carbon atoms,
carbon monoxide,
and combinations thereof.

The ionic rhodium compounds described above are utilized in the present invention as a means of introducing rhodium into the reaction solution and are sometimes referred to as catalyst precursors. Rhodium introduced in this manner together with carbon monoxide, hydrogen, and the modifying ligand described herein form the stable and highly selective rhodium catalysts. Examples of some useful ionic rhodium compounds include [Rh(CO)$_3$(Ph$_3$P)$_2$]BPh$_4$ [Rh(CO)$_3$(Ph$_3$P)$_2$]BF$_4$, [Rh(CO)$_3$(Ph$_3$P)$_2$PF]$_6$, [Rh(COD) (Ph$_3$As)$_2$]ClO$_4$, [Rh(COD) (PhO$_3$P)$_2$]BF$_4$, [Rh(COD) (Ph$_3$As)$_2$PF]$_6$, [RH(CO)$_3$(Ph$_3$Sb)$_2$]BPh$_4$, [Rh(CO)$_3$(Ph$_3$Sb)$_2$]BF$_4$, and [Rh(CO)$_3$(Ph$_3$Sb)$_2$]PF$_6$.

The ionic catalyst and conditions for its use are further described in the copending application Ser. No. 546,227, now abandoned, of Donald E. Morris and the present applicant, filed Apr. 4, 1975, and the disclosure of such application is incorporated herein by reference. Other catalysts which can be utilized in the hydroformylation procedure herein include the rhodium-containing complex catalysts described in Pruett and Smith Pat. 3,527,809, which utilizes various rhodium hydrides and of phosphorous ligands shows a preference for those which are less basic. Further useful hydroformylation catalysts are described in Slaugh and Mullineaux U.S. Pat. No. 3,239,566. The present process can also be utilized to prepare optically active lactic acid by using a hydroformylation catalyst having a soluble metal component with an optically active ligand. Such catalysts involve coordination complexes of a metal selected from rhodium, iridium, and cobalt with optically active phosphine, arsine, stibine or amine ligands of the formula AR′$_3$ wherein A is phosphor, arsenic, antimony or nitrogen, and the R's are individually selected from the organic moieties utilized in the biphyllic ligands described herein, and either the A and/or one or more of the R's is asymmetric and therefore exhibits optical activity. The coordination complex may contain other ligands, for example, carbon monoxide, hydrogen, olefins and diolefins, and halides. The optically active ligand may also be a negatively charged ligand, for example, lactate and glutamate.

The coordination complex is represented by the formula M(An$_w$(olefin)$_x$(CO)$_y$L$z$ wherein M is a metal selected from the group consisting of rhodium, iridium, and cobalt; (An) is a coordinating or non-coordinating anion, such as halide, hydride lactate, acetate, or B(C$_6$H$_5$)$_4$; (olefin) is a mono or diolefin ligand such as ethylene, 1,5-cyclooctadiene, or norbornadiene; L is a neutral ligand most frequently optically active; and w + x + y + z is 4, 5, or 6. Examples of the coordination complexes useful herein include RhH(CO) (cyclohexylanisylmethyl phosphine)$_3$; Rh(1,5-cyclooctadiene) (phenylanisylmethyl phosphine)$_2$ B(C$_6$H$_5$)$_4$, Rh(CO)$_3$ (cyclohexylanisylmethyl phosphine)$_2$ B(C$_6$H$_5$ )$_4$, and Rh$_4$(CO)$_{12}$ (phenylmethylethylphosphine)$_8$.

It has also been found that good yields of optically active aldehydes can be achieved not only in the presence of the above described optically active coordination compounds which are coordination complexes of a metal selected from the group consisting of rhodium, iridium, and cobalt but can also be achieved when the hydroformylation is carried out in the presence of a catalyst that comprises a solution of a metal selected from the group consisting of rhodium, iridium, and cobalt and at least one equivalent of a phosphine and/or arsine ligand per mole of metal, provided that the ligand is optically active. For instance, the catalyst can be prepared by dissolving a soluble metal compound in a suitable solvent together with a ligand wherein the ratio of ligand to metal is at least one equivalent of ligand per mole of metal. Likewise, it has been found that the catalyst can be formed in situ by adding a soluble metal compound to the reaction mass together with the proper amount of optically active ligand to the reaction mass either before or during hydroformylation. Further description of how to conduct hydroformylation reactions to produce asymmetric aldehydes is found in copending application of the present applicant and Arthur J. Solodar Ser. No. 333,269, filed Feb. 16, 1973. The optically active alpha-acetoxypropionaldehyde can then be converted to optically active lactic acid utilizing oxidation and hydrolysis procedures as described herein. Either the d- or the l- form of lactic acid can be produced by appropriate selection of the ligands for the catalyst in the hydroformylation reaction.

In general, the liquid reaction medium employed in the hydroformylation step can contain any solvent which is compatible with the rhodium-containing catalyst and does not react with the vinyl ester feedstock. It is preferred that the solvent be higher boiling than the α-acyloxypropionaldehyde product of the reaction so that a ready separation of the product is possible. Preferred solvents are hydrocarbons and esters.

The feedstock for the hydroformylation reaction step can be any vinyl ester, CH$_2$=CH(OCOR) (where R can be either alkyl or aryl having 1 to 30 carbon atoms). A preferred embodiment of the present invention employs vinyl acetate as the feedstock.

Step 2 — Oxidation of α-Acyloxypropionaldehyde to α-Acyloxypropionic Acid.

In accordance with the present invention, α-acyloxypropionaldehyde produced in the first step of the reaction sequence is oxidized with air or oxygen to α-acyloxypropionic acid.

The reaction may be conducted at a reaction temperature of from $-20°$ C to $200°$ C but is preferably carried out at $10°$ C to $100°$ C.

The oxygen or air used in the reaction may be employed at superatmospheric pressure. Pressures of up to 100 kg/cm$^2$ or higher may be used.

Catalysts such as silver oxide, vanadium salts and oxides, tungsten salts and oxides and other oxidation catalysts can be used to increase the rate of the reaction if desired.

Inert solvents such as hydrocarbons and halocarbons can be employed as diluents to control the exotherm from the reaction if desired.

Step 3 — Hydrolysis of α-Acyloxypropionic Acid to Lactic Acid.

The product from Step 2 of this three-step process is a mixed ester-carboxylic acid, an α-acyloxypropionic acid. In the preferred embodiment of the three-step sequence this material is α-acetoxypropionic acid, derived from vinyl acetate as the starting material for Step 1. The hydrolysis of this mixed ester-carboxylic acid to free lactic acid can be accomplished in the presence of any of the usual acid or base catalysts for ester hydrolysis. Thus, mineral acids, sulphonic acids and resins thereof, carboxylic acids, sodium hydroxide, potassium hydroxide, etc., can all be used to increase the rate of the hydrolysis reaction. The hydrolysis can also be accomplished by heating the aldehyde in the presence of water.

The hydrolysis reaction proceeds in the absence of catalysts. Apparently, the molecule is capable of acting as its own catalyst since it has an acid function attached.

The reaction may be conducted at temperatures of $0°$ C to $300°$ C and preferably from $40°$ C to $220°$ C.

The ratio of reactants can be from 1:1 to 1000:1 of water-acyloxypropionic acid. The order of steps 2 and 3 can be reversed.

The following examples illustrate certain specific embodiments of the invention but are not limitative of the invention.

Example 1

To a 300 ml stainless steel Magnedrive Autoclave was added Rh(cyclooctadiene)(Ph$_3$P)$_2$ BPh$_4$ (0.525 g, 0.50 mmole) and Ph$_3$P (2.6 g, 10. mmoles) as catalyst precursor and acetic acid (100. ml) as solvent. The reactor and contents were pressurized to 13 kg/cm$^2$ with a CO/H$_2$ gas blend (mole ratio = 1. to 1.) and then heated to $100°$ C. Vinyl acetate (21.5 g, 250. mmoles) was pressed into the reactor and the reactor pressure raised to 34 kg/cm$^2$ with this same gas blend. The reactor pressure was maintained at a constant level by employing a pressure regulator which fed the CO/H$_2$ blend from a small storage reservoir. When the CO/H$_2$ blend was no longer being consumed (noted by a constant pressure in the small storage reservoir), the reactor was cooled to $25°$ C and the CO/H$_2$ gas mixture vented. The reactor was disconnected from the CO/H$_2$ gas supply and flushed twice with nitrogen. Air (2 kg/cm$^2$) was pressed into the reactor and the temperature maintained at $25°$ C by the application of cooling water. When the reactor pressure ceased to fall, the reactor was vented and additional air was charged. When the addition of a fresh air supply was followed by no decrease in pressure, water (100 ml) was added to the reactor and system was heated to $150°$ C for 2 hrs. Most of the water and acetic acid were removed from the product solution by distillation. The yield of lactic acid based on reacted vinyl acetate was greater than 60%. Propionic acid (22 mole %) was also recovered. Unexpectedly, no β-hydroxypropionic acid was observed since this would be difficult to separate from lactic acid.

Example 2

The reaction was carried out as described in Example 1 with the exception that, immediately prior to the addition of air, cobaltous acetate (0.15 g in 20 ml of acetic acid was charged to the reactor as a catalyst precursor for the oxidation reaction. Hydrolysis was accomplished at $150°$ C as in Example 1 and the yield of lactic was approximately 70%. Propionic acid was also observed; however, no β-hydroxypropionic acid could be found.

Example 3

The lactic acid synthesis reaction described in Example 2 was employed except that the water (100 ml) added to the reactor contained toluene sulfonic acid (0.1 mmole). Lactic acid, recovered as previously described, was recovered in 74% yield based on charged vinyl acetate.

Example 4

The reaction was performed as described in Example 1 except that water (100 ml) containing sulfuric acid (10$^-$molar) was added to the reactor immediately following the venting of the CO/H$_2$ gas mixture. The reactor was then heated to $200°$ C for 2 hrs and cooled to $25°$ C. Manganese acetate (0.2 g in 20 ml of water) was added and the reactor was pressurized with oxygen (1 kg/cm$^2$) which was replaced as it was consumed. When no more oxygen reacted, the product solution was distilled to remove acetic acid and most of the water. The lactic acid was converted to methyl lactate and distilled. Yield of lactic acid was 57%.

Examples 5 — 9

Examples 5 through 9 were carried out following the techniques of Examples 1, 2, 3, or 4 and employing minor variations as outlined in Table 1.

Example 10

The 300 ml stainless steel Magnedrive Autoclave was charged with the following ingredients: Rh(cyclooctadiene)(Ph$_3$P)$_2$BPh$_4$ (0.105 g, 0.10 mmole) and Ph$_3$P (0.26 g, 1.0 mmole) as catalyst precursor and dioctylphthalate (100 ml) as solvent. The reactor was pressurized to approximately 13 kg/cm$^2$ with the CO/H$_2$ gas blend. Vinyl acetate (43.0 g, 500. mmoles) was forced into the reactor employing the gas blend. The reactor pressure was raised to 33. kg/cm$^2$ and maintained at that pressure by automatic additions to the reactor which replaced gas consumed by the hydroformylation reaction. The reactor was heated to $100°$ C. When the reaction was finished, the contents of the autoclave were analyzed by gas chromatography and found to contain 377. mmoles of alpha-acetoxypropionaldehyde (75. mole % yield). The reaction rate was 2 gram-moles/liter hours.

Beta-acetoxypropionaldehyde, alpha- and beta-acetoxypropanol, and aldol condensation products were not observed. Approximately 95 mole % of the charged vinyl acetate was recovered as either alpha-acetoxypropanolaldehyde, ethyl acetate (usually a trace), and propanaldehyde. Alpha-acetoxypronaldehyde was recovered in high purity by distillation of the product solution at 60-64° C (31. mm).

Example 12

The stainless steel autoclave was charged with vinyl acetate (86 g, 1. mole) as reactant and solvent and Rh(cyclooctadiene)(Ph$_3$P)$_2$BPh$_4$ (0.21 g, 0.2 mmoles) and Ph$_3$P (0.26 g, 1.0 mmole) as catalyst precursor. The reactor and contents were heated to 90° C under 34 kg/cm$^2$ of CO/H$_2$ pressure. When CO/H$_2$ uptake ceased, the reaction was completed as described in Example 1.

Table 1

| Example No. | Technique | Hydroformylation Catalyst Precursor | Pressure and Temperature | Oxidation Catalyst Precursor | Pressure and Temperature | Hydrolysis Catalyst Precursor | Temperature (° C) | Lactic Acid Yield (mole %) |
|---|---|---|---|---|---|---|---|---|
| 5 | Example 1[a] | (Rh(CO)$_2$Cl)$_2$ 0.4 mmole | 35 kg/cm$^2$ 110° C | None | 2 kg/cm$^2$ 125° C | None | 125 | >40 |
| 6 | Example 4 | RhCl (CO) (PH$_3$P)$_2$ 1.0 mmole | 45 kg/cm$^2$ 100° C | Silver oxide | 2 kg/cm$^2$ 25° C | Amberlite IRA 400 | 170 | 53 |
| 7 | Example 2 | HRh (CO) (Ph$_3$P)$_3$ 0.2 mmole | 35 kg/cm$^2$ 95° C | Co(OAc)$_2$ | 4 kg/cm$^2$ 25-30° C | BF$_3$ in methanol | 100 | 65 |
| 8 | Example 3 | Rh$_4$(CO)$_{12}$ 0.1 mmole | 35 kg/cm$^2$ 95° C | Mn (OAc)$_2$ FeCl$_3$ | 2 kg/cm$^2$ 25° C | Toluene sulfonic acid | 190 | 43 |
| 9[b] | Example 1 | (Rh(CO)$_2$Cl)$_2$ 0.4 mmole | 35 kg/cm$^2$ 110° C | None | 2 kg/cm$^2$ 25° C | None | 125 | 41 |

[a]Conduct oxidation and hydrolysis simultaneously.
[b]Vinyl propionate used as reactant.

α-Acetoxypropionaldehyde (5.8 g, 50 mmoles) was dissolved in acetic acid (100 ml) and oxidized by air (1 kg/cm$^2$) at 25° C to α-acetoxypropionic acid in 95 mole % yield in a 360 ml closed, glass reactor. The temperature was maintained by the application of cooling water. The acid was purified by distillation at 126°-128° C (11 mm). Lactic acid was synthesized in a 300 ml autoclave by the hydrolysis of α-acetoxypropionic acid (66. g, 500. mmoles) in water (150 ml) at 150° C. Acetic acid and most of the water was removed by distillation. Overall yield of lactic acid based on reacted vinyl acetate is 65%.

α-Acetoxypropionaldehyde and β-acetoxypropionic acid were identified by elemental analysis, molecular weight, and nuclear magnetic resonance studies. An authentic sample of α-acetoxypropionic acid was prepared by the addition of acetic anhydride to lactic acid [A. Golomb and P. D. Ritchie, J CHEM SOC, 838 (1962)]. The corresponding aldehyde could not be prepared by an independent method.

Example 11

The autoclave was charged with Rh(cyclooctadiene)(Ph$_3$P)$_2$BPh$_4$ (0.210 g, 0.2 mmoles) and Ph$_3$P (0.052 g, 0.2 mmoles) as catalyst precursor and benzene (100 ml) as solvent. The reactor and contents were pressurized to 13 kg/cm$^2$ with the CO/H$_2$ gas blend and heated to 80° C. Vinyl acetate (32.7 g, 380. mmoles) was forced into the reactor as before to start the reaction. When the reaction was complete, the solvent, benzene, was removed by distillation and the α-acetoxypropionaldehyde isolated as before. No β-isomer was observed.

The purified α-acetoxypropionaldehyde was oxidized as before in the presence of cobaltous acetate (2.0 mmoles) and air (2 kg/cm$^2$). A 90 mole % yield of the corresponding carboxylic acid was recovered by distillation.

α-Acetoxypropionic acid (33. g, 250. mmoles) was dissolved in water (150. ml). The solution was charged to the autoclave and heated to 200° C. Acetic acid and water were removed by distillation to give lactic acid in 76% yield based on reacted vinyl acetate.

Example 13

The 300 ml autoclave was charged with the dioctylphthalate solution recovered from the distillation in Example 10. The experiment described in Example 10 was repeated and lactic acid was recovered.

Example 14

Example 2 was repeated employing nonanoic acid as solvent for the synthesis. The yield of lactic acid was very similar.

Example 15

Example 1 was repeated using Rh(cyclooctadiene)(polymeric phosphine)(Ph$_3$P)BP$_4$ as catalyst precursor where the polymeric phosphine is a cross-linked polystyrene co-polymerized with

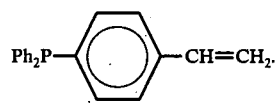

The insoluble rhodium system was filtered from the reaction solution prior to the addition of air. Lactic acid was observed.

Example 16

Example 11 was repeated at 100° C employing triphenylarsine (0.2 mmoles) as the added biphyllic ligand. The overall yield to lactic acid was 60%.

Example 17

Example 11 was repeated at 100° C employing [Rh(cyclooctadiene)(PEt$_3$)$_2$][PF$_6$](0.2mmoles) as the rhodium compound and triethylphosphine (0.4 mmoles) as the added biphyllic ligand. The overall yield to lactic acid was 62%.

Example 18

Example 11 was repeated at 100° C employing (Rh[cyclooctadiene][P(OPh)$_3$]$_2$)BPh$_4$ (0.2 mmoles) as the rhodium compound and triphenylphosphite (0.3 mmoles) as the added biphyllic ligand. The overall yield to lactic acid was 63%.

Example 19

The autoclave was charged with $Co_2(CO)_8$ (10 mmoles), and $Ph_3As$ as catalyst precursor and benzene (100 ml) as solvent. The reactor and contents were pressurized to 35 kg/cm$^2$ with the $CO_2/H_2$ gas blend and heated to 150° C. Vinyl acetate (200 mmole) was forced into the reactor. The alpha-acetoxypropionaldehyde product was isolated as before in yield over 20%, and with a conversion of 43%. The reaction rate was 0.5 gram-mole/liter hour.

It will be noted that in the practice of the present invention it is not necessary to separate the reaction products after each step, but the next step can simply be carried out upon the reaction mixture. Thus the mixture of aldehydes after the first step can be oxidized or hydrolyzed in the reaction mixture, or, if desired, the aldehydes can be distilled from the reaction mixture and the next step can be conducted on the mixture of aldehydes in mass, or with addition of other solvents or diluents. The fact that the oxidation and hydrolysis can be conducted without separating acetoxypropionaldehyde and propionaldehyde from each other may have considerable advantage in avoiding an unnecessary separation step.

In the hydrolysis step, a carboxylic acid is produced, which is acetic acid when vinyl acetate is the starting material. Ordinarily the free acid is obtained, assuming the hydrolysis is not conducted in alcohol or strong bases. Also, decomposition of the beta-acetoxy isomer after the hydroformylation reaction will result in production of acetic acid. The acetic acid thus obtained is a useful article of commerce, and can also be utilized to produce the vinyl acetate starting material. Of course, other carboxylic acids can be used similarly to produce the corresponding vinyl carboxylates. The vinyl acetate can be prepared by reaction of acetic acid with ethylene and oxygen over noble metal catalyst, particularly Group VIII noble metals, oxides, or salts, such as palladium, for example in the form of palladous salts and often with carboxylate ions, such as provided by alkali metal carboxylates, for example sodium acetate. Such preparations are described in the literature and in many patents, for example U.S. Pat. Nos. 3,190,912, and 3,275,680. Thus the acetic acid or other carboxylic acid obtained by hydrolysis or decomposition in the present process can be recycled to the procedure for preparing vinyl acetate or other vinyl carboxylate, and a process involving recycling of acid to a reaction with ethylene and oxygen over noble metal catalyst to obtain vinyl carboxylate, is part of the present invention. Recycling the acid to other preparations of vinyl acetate is also part of the invention such as to the reaction of acetic acid and acetylene, as by passing gaseous acetic acid and acetylene through a carrier such as charcoal impregnated with cadmium or mercury salts at elevated temperature, such as around 200° C.

It has been found that the presently claimed route to lactic acid has advantages in efficiency, cost and suitability compared to other possible routes. Thus the yields in all of the steps are high to excellent, and the necessary reaction conditions and separation conditions are convenient and easily attainable. The advantages could be detailed in terms of yields, conversions, energy useage, efficiency, type of apparatus necssary, etc. However many of these advantages can be summarized in terms of cost, which in some comparisons is particularly meaningful when the processes or their precursor materials may relate to the same original starting materials. Such a comparison can take into account capital costs, as well as costs of raw materials and conversion efficiencies. It has fortunately been found not only that it is possible to obtain good yields in the present process, but that the desired intermediate alpha-acetoxypropionaldehyde has little tendency to take part in further undesired reactions, such as aldol condensations, etc. while the beta-acetoxypropionaldehyde concomitant product is converted to a useful compound, propionaldehyde. Contrary to what might have been expected from the prior art, it has been found possible to convert vinyl acetate to lactic acid in very good yield in an efficient process producing readily separable intermediates and products.

Example 20

Example 11 was repeated except that ethyl vinyl ether was charged to the hydroformylation system. Lactic acid was observed.

What is claimed is:

1. The process of preparing lactic acid which comprises hydroformylating a vinyl carboxylate with carbon monoxide and hydrogen in contact with a hydroformylation catalyst to prepare an alpha-acyloxypropionaldehyde, and oxidizing and hydrolyzing the intermediate to obtain lactic acid.

2. The process of claim 1 in which propionaldehyde is also produced as an intermediate and converted to propionic acid.

3. The process of claim 1 in which a carboxylic acid corresponding to that in the vinyl carboxylate is produced and recycled to produce the vinyl carboxylate starting material.

4. The process of preparing acids from vinyl acetate which comprises hydroformylating vinyl acetate by reaction with carbon monoxide and hydrogen in contact with a hydroformylation catalyst, oxidizing and hydrolyzing the reaction product mixture, and recovering lactic acid, propionic acid and acetic acid.

5. The process of preparing lactic acid which comprises reacting vinyl acetate with carbon monoxide and hydrogen in contact with a hydroformylation catalyst under hydroformylation conditions to produce alpha-acetoxypropionaldehyde in at least 70% yield based on the vinyl acetate, oxidizing and hydrolyzing to convert the alpha-acetoxypropionaldehyde to lactic acid.

6. The process of claim 1 in which the alpha-acyloxypropionaldehyde is not separated from other reaction products prior to oxidizing and hydrolyzing.

7. The process of claim 1 in which optically active lactic acid is prepared by using a hydroformylation catalyst having a soluble metal component with an optically active ligand.

8. The process of claim 1 in which oxygen is utilized for oxidizing the alpha-acyloxypropionaldehyde.

9. The process of claim 8 in which the oxygen is provided by air.

10. The process of claim 1 in which the hydroformylation catalyst is a rhodium complex.

11. The process of claim 1 in which the hydroformylation is conducted in contact with a catalyst provided by a rhodium compound together with at least 2 moles of biphyllic ligand per mole of rhodium, said biphyllic ligand being chosen from the group consisting of triorgano-phosphorous, triorgano-arsenic or triorganoantimony compounds, at a temperature range of from 40° to 160° C; at a total pressure of carbon monoxide and hydrogen of less than about 175 kg/cm² (2500 psi).

12. The process of claim 11 in which the catalyst is a non-halide containing compound.

13. The process of claim 12 in which the catalyst is provided by a cationic rhodium compound.

14. The process of claim 11 in which the vinyl carboxylate is vinyl acetate.

15. The process of claim 11 in which virtually no beta-acyloxypropionaldehyde or beta-acyloxypropionic acid was recovered.

16. The process of claim 11 in which the biphyllic ligand is a triarylphosphine containing from 18 to 60 carbon atoms.

17. The process of claim 11 in which the biphyllic ligand is a triarylarsine containing from 18 to 60 carbon atoms.

18. The process of claim 11 in which the biphyllic ligand is triphenylphosphine.

19. The process of claim 11 in which the vinyl carboxylate is vinyl acetate and the hydroformylation is conducted at a temperature range of from 60° to 130° C; at a total pressure of carbon monoxide and hydrogen of less than about 140 kg/cm² (2000 psi) and greater than 32.5 kg/cm² (460 psi).

20. The process of claim 19 in which the catalyst is a non-halide containing compound.

21. The process of claim 20 in which the catalyst is provided by a cationic rhodium compound.

22. The process of claim 20 in which the biphyllic ligand is a triarylphosphite containing from 18 to 60 carbon atoms.

23. The process of claim 21 in which the cationic rhodium compound is $[Rh(COD)(Ph_3P)_2]BPh_4$.

24. The process of claim 21 in which the cationic rhodium compound is $[Rh(CO)_3(Ph_3P)_2]BPh_4$.

* * * * *

UNITED STATES PATENT OFFICE
CERTIFICATE OF CORRECTION

PATENT NO. : 4,072,709
DATED : February 7, 1978
INVENTOR(S) : Harold Burnham Tinker It is certified that error appears in the above-identified patent and that said Letters Patent are hereby corrected as shown below:

Column 5, line 25, "ligang" should be corrected to read -- ligand --.

Column 6, line 46, "monixide" should be corrected to read -- monoxide --.

Column 9, line 44, "water-acyloxypropionic" should be corrected to read -- water:acyloxypropionic --.

Column 10, line 18, after "acid" there should be inserted a parenthesis -- ) --; line 21, after "lactic" there should be inserted -- acid --; line 36, "($10^-$ molar)" should be corrected to read -- ($10^{-3}$ molar) --.

Column 11, line 38, "β" should be corrected to read -- α --.

Column 12, line 40, "$BP_4$" should be corrected to read -- $BPh_4$ --.

Signed and Sealed this

Twentieth Day of June 1978

[SEAL]

Attest:

RUTH C. MASON
*Attesting Officer*

DONALD W. BANNER
*Commissioner of Patents and Trademarks*